United States Patent [19]

Hauptreif et al.

[11] Patent Number: 5,695,686
[45] Date of Patent: Dec. 9, 1997

[54] BRIGHTENER MIXTURES BASED ON BISSTYRYL COMPOUNDS

[75] Inventors: Manfred Hauptreif, Birkweiler; Norbert Leppert, Speyer; Karl-Heinz Etzbach, Frankenthal; Helmut Reichelt, Neustadt; Peter Raatz; Manfred Herrmann, both of Ludwigshafen, all of Germany

[73] Assignee: BASF Aktiengesellschaft, Ludwigshafen, Germany

[21] Appl. No.: 605,076

[22] PCT Filed: Sep. 2, 1994

[86] PCT No.: PCT/EP94/02914

§ 371 Date: Mar. 13, 1996

§ 102(e) Date: Mar. 13, 1996

[87] PCT Pub. No.: WO95/08017

PCT Pub. Date: Mar. 23, 1995

[30] Foreign Application Priority Data

Sep. 13, 1993 [DE] Germany .................. 43 30 968.2

[51] Int. Cl.$^6$ .................................................... D06C 3/12
[52] U.S. Cl. ........................................ 252/301.21; 558/411
[58] Field of Search ........................... 558/411; 252/301.21

[56] References Cited

U.S. PATENT DOCUMENTS

| | | | |
|---|---|---|---|
| 4,778,622 | 10/1988 | Guglielmetti et al. | 252/301.21 |
| 4,867,906 | 9/1989 | Guglielmetti et al. | 252/301.21 |
| 5,053,055 | 10/1991 | Fringeli et al. | 252/301.21 |
| 5,072,016 | 12/1991 | Guglielmetti et al. | 252/301.21 |

FOREIGN PATENT DOCUMENTS

| | | |
|---|---|---|
| 238446 | 3/1987 | European Pat. Off. . |
| 321 393 | 11/1988 | European Pat. Off. . |
| 2745449 | 3/1979 | Germany . |

*Primary Examiner*—Melissa Bonner
*Attorney, Agent, or Firm*—Oblon, Spivak, McClelland, Maier & Neustadt, P.C.

[57] ABSTRACT

Brightener mixtures containing from 75% by weight to 100% by weight, based on the weight of the mixture, of the bisstyryl compounds of the formulae I and II

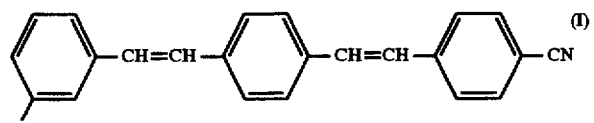

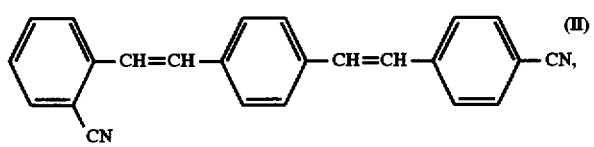

in a weight ratio from 10:90 to 70:30, formulations containing the novel mixtures, and also their use for optically brightening synthetic, semisynthetic or natural polymer materials.

20 Claims, No Drawings

BRIGHTENER MIXTURES BASED ON BISSTYRYL COMPOUNDS

The present invention relates to novel brightener mixtures containing from 75% by weight to 100% by weight, based on the weight of the mixture, of the bisstyryl compounds of the formulae I and II

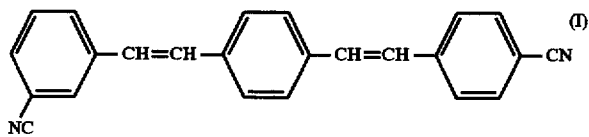

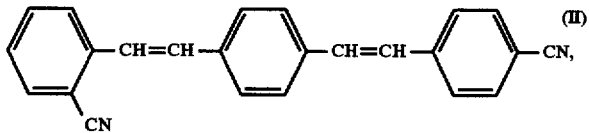

in a weight ratio from 10:90 to 70:30, formulations containing the novel mixtures, and also their use for optically brightening synthetic, semisynthetic or natural polymer materials.

EP-A-238 446 and EP-A-321 393 disclose mixtures of optical brighteners containing the abovementioned bisstyryl compounds I and II in the weight ratios 80.25:19.75 and 80:20. However, it has been found that these mixtures have disadvantages in their application properties.

GB-A-2 200 660 describes brightener mixtures containing from 51 to 98.5% by weight of the bisstyryl compound I and from 48.5 to 1% by weight of bisstyrene compound II.

It is an object of the present invention to provide novel brightener mixtures based on bisstyryl compounds which shall be simple to obtain and have advantageous application properties, in particular high whiteness.

We have found that this object is achieved by the brightener mixtures more particularly described at the beginning.

The novel brightener mixtures, in each case based on the weight of the mixture, contain from 75 to 100% by weight, preferably from 80 to 100% by weight, in particular from 85 to 100% by weight, of the bisstyryl compounds of the formulae I and II.

Of particular industrial interest are brightener mixtures containing, based on the weight of the mixture, from 85 to 90% by weight of the bisstyryl compounds of the formulae I and II.

As remainders (to 100% by weight) the brightener mixtures of the invention may generally additionally contain compounds of the formulae III and/or IV

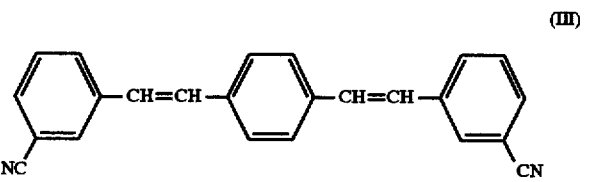

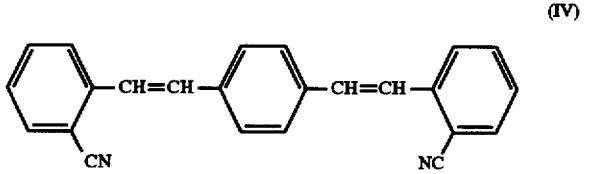

In the brightener mixtures of the invention the bisstyryl compounds of the formulae I and II are present in a weight ratio from 10:90 to 70:30, preferably from 20:80 to 60:40, and in particular from 30:70 to 60:40.

Of particular industrial interest are brightener mixtures in which the bisstyryl compounds of the formulae I and II are present in a weight ratio from 40:60 to 50:50, in particular about 45:55.

The novel brightener mixtures can be prepared for example by mixing the individual components in the appropriate weight ratio. The individual components can be obtained in a conventional manner. For example, terephthalaldehyde can be reacted with alkyl cyanophosphonates in a basic medium in an inert organic diluent.

The present invention further provides brightener formulations containing water and, in each case based on the weight of the formulation, from 3 to 25% by weight, preferably from 5 to 15% by weight, of the above-defined brightener mixture and also from 5 to 60% by weight, preferably from 5 to 52% by weight, of auxiliaries.

Suitable auxiliaries include for example anionic or nonionic dispersants from the class of the ethylene oxide adducts with fatty alcohols, higher fatty acids or alkylphenols or ethylenediamineethylene oxide-propylene oxide adducts, or dispersants as described in DE-A-2 745 449, copolymers of N-vinylpyrrolidone with 3-vinylpropionic acid, water retention aids, such as ethylene glycol, glycerol or sorbitol, or biocides.

A preferred brightener formulation, in addition to water, contains in each case, based on the weight of the formulation, from 3 to 25% by weight, preferably from 5 to 15% by weight, of the above-defined brightener mixture, from 3 to 12% by weight of anionic or nonionic dispersant, from 1 to 15% by weight of copolymers of N-vinylpyrrolidone with 3-vinylpropionic acid and from 1 to 25% by weight of further auxiliaries (eg. water retention aids or biocides).

The brightener mixtures of the invention are advantageously suitable for optically brightening synthetic, semisynthetic or natural polymer materials, preferably polyester and in particular polyester fabrics. They combine a low fixing or exhaust temperature with advantageous application properties. They are also high yielding.

The Examples which follow illustrate the invention.

PREPARATION OF BRIGHTENER MIXTURE a) To a mixture in 1100 ml of N,N-dimethylformamide of 201 g (1.47 mol) of terephthalaldehyde (98.45% by weight) and 402.7 g (1.47 mol) of diethyl 3-cyanobenzylphosphonate (91.7% by weight) were added over 4 h at 30° C. 279.8 g (1.54 mol) of 30% strength by weight methanolic sodium methoxide solution. This was followed by stirring at 30° C. for 2 h and then 434.9 g (1.54 mol) of diethyl 4-cyanobenzylphosphonate and finally a further 279.8 g (1.54 mol) of 30% strength by weight methanolic sodium methoxide solution were added. After the reaction solution had subsequently been stirred at 30° C. for 4 h, it was cooled down to 25° C., and the resulting precipitate was filtered off with suction, washed three times with 500 ml of methanol each time and once with 1650 ml of water and dried to leave 335 g of a mixture containing 284 g of the compound of formula

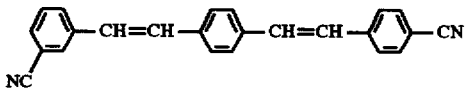

and 34 g of the compound of formula

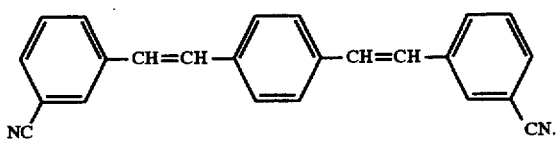

b) To a mixture in 1100 ml of N,N-dimethylformamide of 201 g (1.47 mol) of terephthalaldehyde (98.45% by weight) and 395.7 g (1.47 mol) of diethyl 2-cyanobenzylphosphonate (94% by weight) were added over 3 h at 30° C. 279.8 g (1.54 mol) of 30% strength by weight methanolic sodium methoxide solution. This was followed by stirring at 30° C. for 1 h and then 434.9 g (1.54 mol) of diethyl 4-cyanobenzylphosphonate and finally a further 279.8 g (1.54 mol) of 30% strength by weight methanolic sodium methoxide solution were added. After the reaction solution had subsequently been stirred at 30° C. for 1 h, it was cooled down to 25° C., and the resulting precipitate was filtered off with suction, washed three times with 500 ml of methanol each time and once with 1650 ml of water and dried to leave 332 g of a mixture containing 279 g of the compound of formula

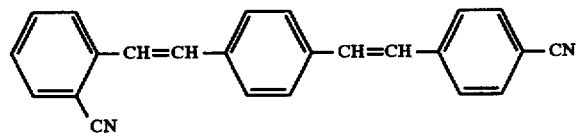

and 49 g of the compound of formula

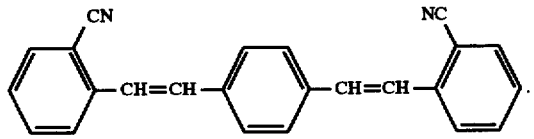

c) The components described under a) and b) were each mixed in a weight ratio of 30:70 (Example 1), 45:45 (Example 2) and 68:32 (Example 3).

PREPARATION OF FORMULATION (General Method)

11 parts by weight of the brightener mixture described under c), 35% by weight of the dispersant described in Example 13 of DE-A-2 745 449, 5 parts by weight of the copolymer of N-vinylpyrrolidone with 3-vinylpropionic acid, 12 parts by weight of glycerol, 0.5 part by weight of 30% strength by weight aqueous formaldehyde solution and 68 parts by weight of water are milled in a stirred ball mill at pH 8 until the particle size of the brightener is less than 5 µm. The resulting mill base comprises thin-liquid dispersions which have a long storage life and are free of sedimentation.

General Dyeing Method a) HT process

Polyester fabric is introduced at 55° C. into a dyebath which contains x% by weight of brightener formulation (based on the weight of the fabric) and 1 g/l of the sodium salt of a condensation product of 2-naphthalenesulfonic acid and formaldehyde and whose pH has been adjusted with acetic acid to 5–5.5. The bath is then heated over 30 minutes to 130° C. and held at that temperature for a further 30 minutes. Thereafter the fabric is rinsed and dried.

The concentration of brightener formulation (containing the respective brightener mixture of Examples 1 to 3) was in each case 0.22% by weight and 1.0% by weight. Good brightening effects were obtained in all cases.

b) Thermosol process

Polyester fabric is padded at room temperature with an aqueous liquor containing x g/l of brightener formulation. The wet pickup is 60%. The fabric is then dried and set at 190° C. for 30 seconds.

The concentration of brightener formulation (containing the respective brightener mixtures of Examples 1 to 3) was in each case 2.7 g/l and 10 g/l. Good brightening effects were obtained in all cases.

We claim:

1. A brightener mixture comprising the bisstyryl compounds of formulas I and II

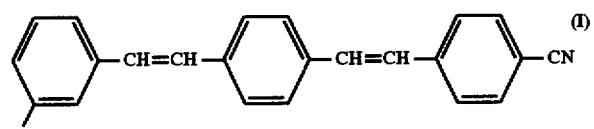

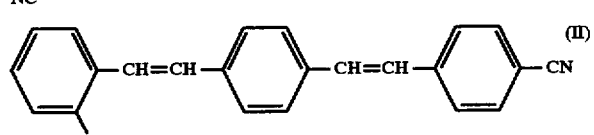

in a weight ratio of I:II of 10:90 to 70:30.

2. The brightener mixture of claim 1, wherein said mixture comprises 75–100% by weight, based on the weight of said mixture, of said bisstyryl compounds of formula I and II.

3. The brightener mixture of claim 1, wherein said mixture comprises 80–100% by weight, based on the weight of said mixture, of said bisstyryl compounds of formulas I and II.

4. The brightener mixture of claim 1, wherein said mixture comprises 85–100% by weight, based on the weight of said mixture, of said bisstyryl compounds of formulas I and II.

5. The brightener mixture of claim 1, wherein said weight ratio of I:II is 20:80 to 60:40.

6. The brightener mixture of claim 1, wherein said weight ratio of I:II is 30:70 to 60:40.

7. The brightener mixture of claim 1, further comprising water and auxiliaries.

8. The brightener mixture of claim 7, wherein said mixture comprises 3–25% by weight of said bisstyryl compounds of formulas I and II, and 5–60% by weight of said auxiliaries, all based on the weight of said mixture.

9. The brightener mixture of claim 1, further comprising:
   3–12% by weight of anionic or nonionic dispersants,
   1–15% by weight of copolymers of N-vinylpyrrolidone with 3-vinylpropionic acid, and
   1–25% by weight of auxiliaries selected from the group consisting of water retention aids, biocides and mixtures thereof,
   wherein said mixture comprises 3–25% by weight of said bisstyryl compounds of formula I and II, all based on the weight of said mixture.

10. A method of optically brightening a polymer, comprising contacting a polymer with the brightener mixture of claim 1.

11. A method of optically brightening a polymer, comprising contacting a polymer with the brightener mixture of claim 8.

12. A method of optically brightening a polyester, comprising contacting a polyester with the bright tenet mixture of claim 6.

13. A method of making a brightener composition, comprising:

mixing bisstyryl compounds of the formulas I and II

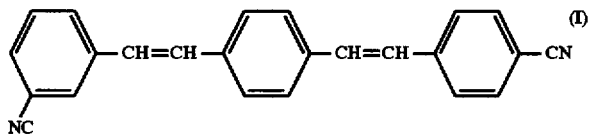

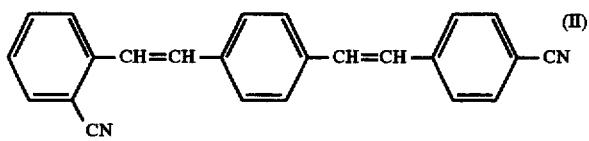

in a weight ratio of I:II of 10:90 to 7:30, to form a brightener mixture.

14. The method of claim 13, further comprising mixing water with said brightener mixture, thereby forming a brightener formulation, wherein an amount of said brightener mixture mixed is 3–25% by weight, based on the weight of said brightener formulation.

15. The method of claim 14, further comprising mixing said brightener formulation with a bath, to prepare a brightener bath, and contacting said polymer with said brightener bath.

16. The method of claim 13, wherein an amount of the bisstyryl compounds of the formulas I and II mixed is 80–100% by weight, based on the weight of said brightener mixture, and said weight ratio of I:II is 20:80 to 60:40.

17. The method of claim 14, wherein said brightener formulation is prepared by mixing said water, 3–25% by weight of said brightener mixture, and 5–60% by weight of auxiliaries, all based on the weight of said brightener formulation.

18. The product produced by the method of claim 13.
19. The product produced by the method of claim 14.
20. The product produced by the method of claim 16.

* * * * *